United States Patent [19]

Chan et al.

[11] 4,345,084
[45] Aug. 17, 1982

[54] UNSATURATED EICOSANOIC ACIDS

[75] Inventors: Ka-Kong Chan, Hopatcong; George W. Holland; Perry Rosen, both of North Caldwell, all of N.J.

[73] Assignee: Hoffmann-La Roche Inc., Nutley, N.J.

[21] Appl. No.: 278,531

[22] Filed: Jun. 29, 1981

[51] Int. Cl.$^3$ .................... C07D 263/10; C07C 57/52; C07C 57/00

[52] U.S. Cl. ..................... 548/237; 548/239; 560/205; 560/219; 560/227; 560/183; 560/184; 568/448; 568/849; 260/465.6; 260/465.7; 570/136; 570/135; 424/272; 424/314; 424/317

[58] Field of Search ................................. 548/237, 239

[56] References Cited

FOREIGN PATENT DOCUMENTS 51-113817 10/1976 Japan .................................. 548/237
52-85167 7/1977 Japan .................................. 548/237

OTHER PUBLICATIONS

Fujita, et al, Chemical Abstracts, vol. 86, 121570v, 1977.
Fujita, et al, Chemical Abstracts, vol. 88, 121462c, 1976.
Lindlar, H., Helvetica Chimica Acta., vol. 35, pp. 446–450, 1952.
Isler, et al, Helvetica Chimica Acta, vol. 32, pp. 489–505, 1949.

*Primary Examiner*—Donald G. Daus
*Assistant Examiner*—Sharon A. Gibson
*Attorney, Agent, or Firm*—Jon S. Saxe; George M. Gould; William H. Epstein

[57] ABSTRACT

Unsaturated eicosanoic acids and derivatives thereof which inhibit the synthesis of SRS-A are useful for treating and preventing asthma and allergic responses caused by SRS-A as well as useful in inhibiting inflammation.

9 Claims, No Drawings

UNSATURATED EICOSANOIC ACIDS

BACKGROUND OF INVENTION

The material SRS-A (slow reacting substance of anaphylaxis) like histamine is released from the cells of mammals during an allergic reaction. The SRS-A excreted by the cells contracts smooth muscle tissue producing such allergic responses as asthmatic attacks. Thus, there has been a great need for pharmaceuticals which inhibit the synthesis of SRS-A to prevent its release by the cells during an allergic response.

Conventional anti-allergic drugs such as antihistamines, while effective in neutralizing the histamine produced during an allergic response, have been ineffective in neutralizing or antagonizing the effects of SRS-A. This has limited the usefulness of these antihistamines as anti-asthmatic agents. Therefore, it has long been desired to develop compounds which will specifically inhibit the synthesis of SRS-A by the cells of a mammal to prevent its release during an allergic response and prevent the conditions associated with such an allergic response.

SUMMARY OF THE INVENTION

In accordance with this invention, we have discovered that compounds of the formula:

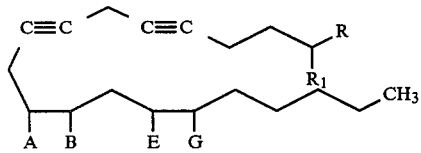

wherein R is —COOR', or

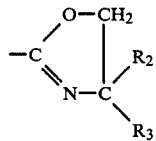

$R_1$ is hydrogen or fluoro; A and B are individually hydrogen or taken together form a carbon to carbon bond with a cis configuration; E and G are individually hydrogen or taken together form a carbon to carbon bond with a cis configuration with the proviso that at least one of A and B taken together or E and G taken together form a carbon to carbon bond with a cis configuration; and R', $R_2$ and $R_3$ are hydrogen or lower alkyl; and

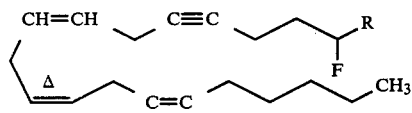

where R is as above and Δ designates a double bond having a cis configuration, or pharmaceutically acceptable salts thereof inhibit the synthesis of SRS-A and are useful for treating asthma or allergic responses caused by SRS-A. The compounds of formulae I and II also inhibit inflammation.

DETAILED DESCRIPTION

The term "halogen" as used herein includes all forms of halogens, i.e. chlorine, fluorine, bromine and iodine with chlorine and bromine being preferred. The term "lower alkyl" designates any saturated straight or branched aliphatic hydrocarbon group containing from 1 to 7 carbon atoms such as methyl, ethyl, isopropyl, or propyl, butyl, t-butyl, etc. The term "lower alkoxy" includes any lower alkoxy group containing from 1 to 7 carbon atoms, such as methoxy, isopropoxy, ethoxy, etc.

The term "lower alkanoyloxy" designates residues of saturated aliphatic acids containing from 2 to 7 carbon atoms. Among these lower alkanoyloxy groups are included acetoxy, pivalyloxy, etc. As used herein, the term "aryl" signifies mononuclear aromatic hydrocarbon groups such as phenyl which can be unsubstituted or substituted in one or more positions with a lower alkyl and polynuclear aryl group such as naphthyl anthyryl which can be unsubstituted or substituted with one or more of the lower alkyl groups. The preferred aryl groups are phenyl or tolyl. The conventional hydrolyzable ether group utilized to protect an —OH group can be any conventional ether which hydrolyzes to a hydroxy group upon ether hydrolysis. Among the preferred ether protecting groups are included tetrahydropyranyl, t-butyl and aryl methyl ethers. Among the preferred aryl methyl ethers are benzyl.

The compounds of formulae I and II where R is —COOH can be used in accordance with this invention in their salt form. Any conventional pharmaceutically acceptable basic salts of the compound of formulae I and II can be utilized. Among the conventional basic salts which can be utilized are included metal ions e.g. aluminium, alkali metal salts such as sodium or potassium, alkaline earth metal salts such as calcium or magnesium, and ammonium or substituted ammonium salts for example those from lower alkylamines, such as triethylamine, hydroxy-lower alkylamines such as 2-hydroxyethylamine, tris(hydroxymethyl)aminomethane, bis-(2-hydroxyethyl)-amine or tris-(2-hydroxyethyl)-amine, cycloalkylamines such as bicyclohexylamine, or from procaine, dibenzylamine, N,N-dibenzylethylenediamine, 1-ephenamine, N-ethylpiperidine, N-benzyl-α-phenethylamine, dehydroabietylamine, N,N'-bis-dehydrobietylethylenediamine, or bases of the pyridine type such as pyridine, collidine or quinoline. These salts can be formed from the compounds of formulae I and II where R is —COOH by treating this acid in a conventional manner with a base such as an metal hydroxide, ammonium hydroxide or an amine base.

The compounds of formulae I or II, as well as their pharmaceutically acceptable salts, are inhibitors of SRS-A synthesis and are useful as in treating or preventing and other allergic responses caused by SRS-A, expecially broncoconstriction. The compounds of this invention are also useful as antiinflammatory agents.

The compounds of formulae I or II, as well as salts thereof or compositions containing effective amounts of these amounts of these compounds are useful for treating or preventing asthma or other allergic responses to SRS-A or as antiinflammatory agents. These compounds can be administered by methods well known in the art. They can be administered, either singly or with other pharmaceutical agents, e.g., antagonists or mediators of anaphylaxis such as antihistamines, or antiasthmatic steroids such as prednisone and prednisolone, orally, parenterally or by inhalation, e.g., in the form of an aerosol, micropulverized powder or nebulized solution. For oral administration they can be administered in the form of pills, tablets, capsules, e.g., in admixture with talc, starch, milk sugar or other inert ingredients, i.e. pharmaceutically acceptable carriers, or in the form of aqueous solutions, suspensions, encapsulated suspensions, gels, elixirs or aqueous alcoholic solutions, e.g., in admixture with sugar or other sweetening agents, flavorings, colorants, thickeners and other conventional pharmaceutical excipients. For parenteral administration, they can be administered in solutions or suspension, e.g., as an aqueous or peanut oil solution or suspension using excipients and carriers conventional for this mode of administration. For administration as aerosols, they can be dissolved in a suitable pharmaceutically acceptable solvent, e.g., ethyl alcohol or water or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, i.e., one, which on activation, releases a predetermined effective dose of the aerosol composition.

In practicing the method of the invention, the dose of compounds of formulae I or II or their salts to be administered and the frequency of administration will be dependent on the potency and duration of activity of the particular compound to be administered and on the route of administration, as well as the severity of the condition, age of the mammal to be treated, etc. Doses of compounds of formulae I or II or salts thereof contemplated for use in practicing the method of the invention are about 0.001 to about 50 mg per kilogram of body weight per day, preferably about 0.01 to about 5 mg per kilogram of body weight per day, either as a single dose or in divided doses administered orally.

The compound of formula I where $R_1$ is hydrogen and R is other than an ester group is prepared by reacting a compound of the formula:

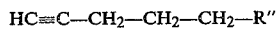

HC≡C—CH$_2$—CH$_2$—CH$_2$—R''      IV wherein R'' is —COOH or

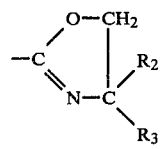

and $R_2$ and $R_3$ are as above, with a compound of the formula:

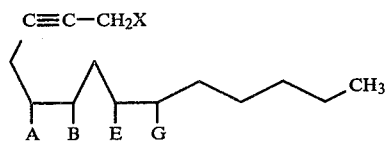

V wherein X is halogen, A, B, and E and G are above with the proviso that at least one of A and B taken together or E and G taken together form a carbon to carbon bond with a cis configuration.

This reaction is carried out by first converting the compound of formula IV to the corresponding magnesium halide which has the formula:

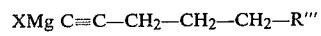

XMg C≡C—CH$_2$—CH$_2$—CH$_2$—R'''      VII wherein X is as above; and R''' is —COOMgX, or COOY or

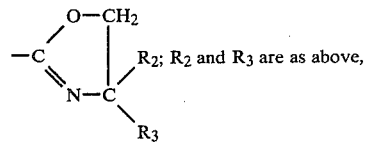

$R_2$; $R_2$ and $R_3$ are as above, and Y is an alkali metal cation.

This reaction is carried out by treating the compound of formula IV with a lower alkyl magnesium halide such as ethyl magnesium halide. Generally, this reaction is carried out in the presence of an inert organic solvent. Any conventional inert organic solvent can be utilized. Among the preferred solvents are the ether solvents such as tetrahydrofuran, dioxane, diethyl ether, etc. In carrying out this reaction, temperatures and pressures are not critical, and this reaction can be carried out at room temperature and atmospheric pressure. Generally, temperatures of from −50° C. to +100° C. are preferred with temperatures of from −10° C. to +50° C. being especially preferred. Furthermore, this reaction is carried out under an inert atmosphere. Any conventional inert gas can be utilized to create the inert atmosphere. Generally, this reaction is carried out in the presence of argon, nitrogen, helium or krypton.

In preparing the compound of formula VII where R''' is COOY, the compound of formula IV is first treated with an alkali or alkaline earth metal base such as lithium or sodium hydroxide to form the acid salt prior to treatment with a lower alkyl magnesium halide to form the magnesium halide of formula VII. Any conventional method of converting an organic acid to its alkali metal or alkaline earth metal salt form can be used in this reaction.

The compounds of formula I where $R_1$ is hydrogen is formed by reacting the compound of formula V with the compound of formula VII. Generally, this reaction is carried out in the presence of a copper or copper-containing catalyst. Any conventional copper-containing catalyst such as a copper salt can be utilized in carrying out this reaction. The preferred copper salt is Copper I cyanide. Generally, this reaction is carried out in an inert atmosphere utilizing the same conditions as described in connection with the formation of the compound of formula VII from the compound of formula IV. In fact, it is preferred to carry out this reaction in the same reaction medium that was utilized for forming the compound of formula VII from the compound formula IV without isolating the compound of formula VII from the reaction medium.

The compound of formula I where $R_1$ is fluorine is formed by first reacting a compound:

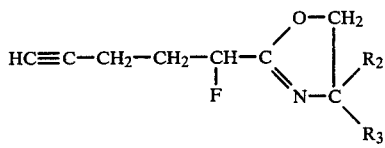
IV-A where $R_2$ and $R_3$ are as above with a compound of the formula V. This reaction is carried out in the same manner as described in connection with the conversion of the compound IV, by reaction with the compound of formula V, to the compound of formula I where $R_1$ is hydrogen. In the conversion of the compound of IV-A to the compound of formula I where $R_1$ is fluorine, the compound of formula IV-A is first converted, as described in connection with the compound formula IV to the compound of formula VII to a compound of the formula:

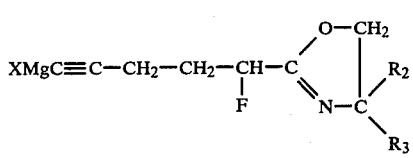
VII-A where X, $R_2$ and $R_3$ are as above by reaction with a lower alkyl magnesium halide.

The compound of formula VII-A by reaction with the compound of formula V is converted to a compound of the formula:

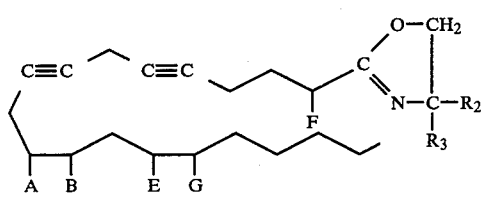
I-B wherein A and B and E and G are as above, with that at least one of A and B or E and G taken together form a carbon to carbon bond with a cis configuration; and $R_2$ and $R_3$ are as above.

The compound of formula I-B or the compound of formula I where R is other than —COOR can be converted to the corresponding free acid:

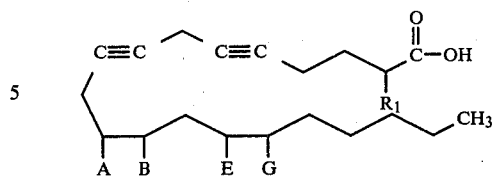
I-C wherein $R_1$, A and B and E and G are as above, with the proviso that at least one of A and B or E and G taken together form a carbon to carbon bond with a cis configuration, by hydrolysis with a dilute aqueous mineral acid such as hydrochloric acid, sulfuric acid, etc. Any conventional method of hydrolysis with a dilute aqueous mineral acid can be utilized to effect this conversion. The compound of formula I-C or the compound of formula I where R is COOH can be esterified by any conventional means of esterification such as reaction with a lower alkyl halide to produce the ester of

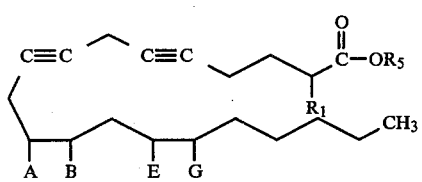
I-D wherein $R_1$, A and B and E and G are as above, with the proviso that at least one of A and B or E and G taken together form a carbon to carbon bond with a cis configuration and $R_5$ is lower alkyl.

In carrying out these hydrolysis and esterification reactions, it is generally preferred to carry out these reactions in the presence of an inert gaseous atmosphere.

In accordance with this invention, the compound of formula V where A and B and E and G form carbon to carbon bonds having a cis configuration, i.e. a compound of the formula:

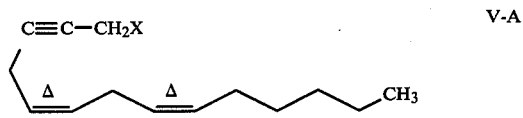
V-A wherein X is as above and Δ designates a cis configuration about the double bond is produced from a compound of the formula:

$$HO-CH_2-C\equiv C-CH_2-C\equiv C-CH_2-CH_2-CH_2-CH_2-CH_3 \quad \text{IX}$$

via the following intermediates

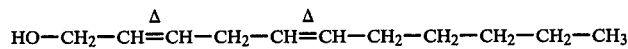
X

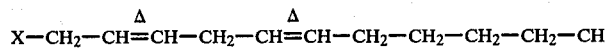
XI

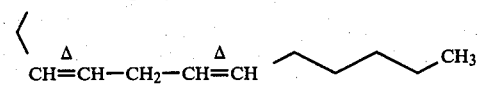
XII wherein X is as above; and R₉ is hydrogen or taken together with its attached oxygen atom forms an ether protecting group, preferably tetrahydropyranyl, and Δ is as above.

The compound of formula IX is converted to the compound of formula X by hydrogenation in the presence of a selective hydrogenation catalyst. Any catalyst which selectively reduces only the triple bond (acetylene linkage) to a double bond can be utilized in carrying out this conversion. Among the preferred selective hydrogenation catalysts are the palladium catalysts which contain a deactivating material such as lead, lead oxide or sulfur. Among the preferred selective hydrogenation catalysts are included the palladium-lead catalysts of the type disclosed in Helv. Chim. Acta. 35 pg. 446 (1952) and U.S. Pat. No. 2,681,938 to Lindlar. These catalysts are commonly known as Lindlar catalysts. The hydrogenation of the compound of the formula IX using a selective hydrogenation catalyst produces a double bond containing a cis configuration. Therefore, selective hydrogenation of the compound of formula IX containing two acetylenic linkages produces two double bonds having a cis configuration.

The compound of formula X is converted to the compound of formula XI by treating the compound of formula X with a halogenating agent. Any conventional halogenating agent can be utilized in effecting this conversion. Among the preferred halogenating agents are carbontetrachloride and triphenylphosphine. Any of the conditions conventional in halogenating a hydroxy group with conventional halogenating agents can be utilized in carrying out this reaction.

The compound of formula XI can be converted to the compound of formula XII by treating the compound of formula XI with a compound of the formula

HC≡C—CH₂—OR₉    XIII wherein R₉ is hydrogen or an ether protecting group.

In carrying out this reaction, the compound of formula XIII is converted to its corresponding magnesium halide of the formula:

XMgC≡C—CH₂R₁₃    XIII-A wherein R₁₃ is —OR₉ or —OMgX; X is as above; and R₉' is an ether protecting group, by reacting the compound of formula XIII with a lower alkyl magnesium halide. Any conventional method of forming a magnesium halide salt such as described hereinbefore in connection with the formation of a compound of formula VII can be utilized in this conversion. On the other hand, the compound of formula XIII can be converted to a compound of the formula:

YC≡C—CH₂—R₁₃'    XIII-B where R₁₃' is —OR₉ or —OY; Y is an alkali metal cation preferably lithium; and R₉' is as above, by reaction with an alkali metal alkyl such as n-butyl lithium. In carrying out this reaction any conventional method of forming an alkali metal acetalide can be used to convert the compound of formula XIII to a compound of formula XIII-B. The compound of formula XII is produced by reacting the compound of formula XIII-A or XIII-B with the compound of formula XI. Wherein R₉ in the compound of formula XIII is hydrogen, the compound of formula XIII-A is formed where R₁₃ is —OMgX and the compound of formula XIII-B is formed where R₁₃ is —OY. In forming the compound of formulae XIII-A and XIII-B, an inert atmosphere, as described hereinbefore, is generally used.

The compound of formula XI is converted to the compound of formula XII by reaction with the compound of formulae XIII-A or XIII-B. This reaction is carried out by utilizing the same procedure as described hereinbefore in connection with reacting the compound of formula V with the compound of formula VII to produce a compound of formula I. In general, this reaction is carried out under an inert atmosphere. The compound of formula XII where OR₉ forms an ether protecting group is converted to the compound of formula XII where R₉ is hydrogen by conventional ether cleavage such as hydrolysis. Generally, it is preferred to carry out this hydrolysis by treatment with a strong organic acid such as p-toluene sulfonic acid.

The compound XII where R₉ is hydrogen is converted to the compound of formula V-A by treating the compound of formula XII where R₉ is hydrogen with a halogenating agent such as phosphorous tribromide in pyridine utilizing conditions conventionally used with respect to these halogenating agents.

Compounds of formula V where A and B are hydrogen and E and G form a carbon to carbon bond having a cis configuration, i.e. compounds of the formula:

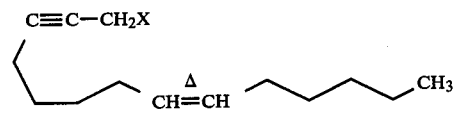
V-B wherein Δ and X are as above, are prepared from the reaction product of

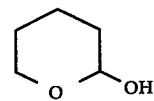
VI

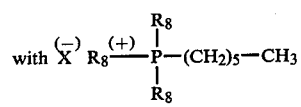
XIV wherein R₈ is aryl and X is as above, via the following intermediates:

HOCH₂—CH₂—CH₂—CH₂—CH=CH—CH₂—CH₂—CH₂—CH₂—CH₃    XV

XCH₂—CH₂—CH₂—CH₂—CH=CH—CH₂—CH₂—CH₂—CH₂—CH₃    XVI

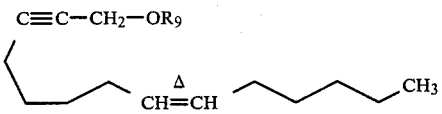

XVII wherein Δ and R$_9$ are as above.

The compoud of formula VI is condensed with the compound of formula XIV to produce the compound of the formula XV by means of a Wittig reaction. Any of the conditions conventionally used in Wittig reactions can be used in carrying out this reaction. Generally this reaction is carried out in the presence of an ether solvent and a base. Among the preferred bases are the silyl bases such as sodium bistrimethylsilylamide. The Wittig reaction produces the double bond in the compound of formula XV with a predominantly cis configuration.

The compound of formula XV is converted to the compound of formula XVI by treating the compound of formula XV with a halogenating agent such as described hereinbefore. The preferred halogenating agent for use in this reaction is phosphorous tribromide in the presence of an organic basic solvent such as pyridine. Any of the conditions conventionally used with these halogenating agents can be utilized in carrying out this reaction.

The compound of formula XVI is converted to the compound XVII by reacting the compound of formula XVI with the compound of formula XIII-B. This reaction is carried out in the presence of an organic solvent at a temperature of from −70° C. to 25° C. with temperatures of from −30° C. to +25° C. being preferred. The preferred solvents in this reaction are tetrahydrofuran, hexamethyl phosphoric acid triamide mixtures of these, as well as diethylether dioxane, etc.

Where R$_9$ in the compound of formula XIII is —OY, the compound of formula XVII is produced where R$_9$ is hydrogen. On the other hand, if R$_9$ in the compound of formula XIII-B is an ether-protecting group, the compound of formula XVII is formed where R$_9$ is an ether-protecting group. This ether-protecting group can be converted to the free hydroxy compound of formula XVII, i.e. the compound of formula XVII where R$_9$ is hydrogen, by acid hydrolysis. Any conventional method of hydrolyzing an ether group to the corresponding hydroxy compound can be utilized. Among the preferred method is by the use of a strong organic acid such as p-toluene sulfonic acid in an inert organic solvent such as methyl alcohol.

The compounds of formula XVII where R$_9$ is hydrogen is converted to the compound of formula V-B by halogenation. Any conventional method of halogenation such as by use of conventional halogenating agents such as phosphorus tribromide can be utilized to carry out this reaction.

The compound of formula V wherein A and B form a cis double bond and E and G are hydrogen, i.e. a compound of the formula

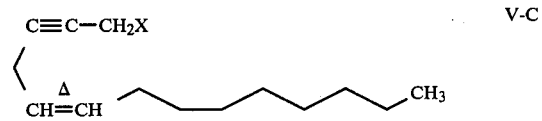

V-C where Δ and X are as above, can be prepared from a compound of the formula $$HOCH_2-C\equiv C-CH_2-CH_2-CH_2-CH_2-CH_2-CH_2-CH_2-CH_3 \quad \text{XVIII}$$

via the following intermediates

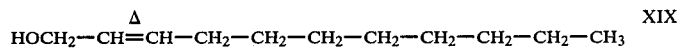

XIX

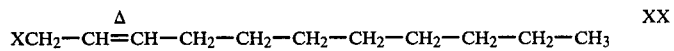

XX

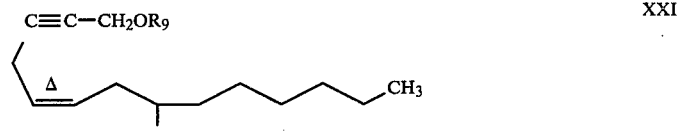

XXI wherein Δ, X and R$_9$ are as above.

The known compound of formula XVIII is converted to the compound of formula XIX by selective hydrogenation in the same way as hereinbefore described in connection with the conversion of the compound of the formula IX to a compound of the formula X. The double bond produced by selective hydrogenation in the compound of formula XIX has a cis configuration. The compound of formula XIX is converted to the compound of formula XX by halogenation such as described hereinbefore in connection with the halogenation of formula X to the compound of formula XI. The compound of formula XX is converted to the compound of formula XXI by reaction with the compound of formula XIII-A or XIII-B in the same manner as described in connection with the conversion of the compound of formula XI to the compound of formula XII. The compound of formula XXI where R$_9$ is hydrogen is converted to the compound of formula V-C by halogenation in the same manner as disclosed in connection with the conversion of the compound of formula XVII to the compound of formula V-B. Where R$_9$ is an ether-protecting group in the compound of formula XXI this ether protecting group is hydrolyzed by acid hydrolysis to form the corresponding hydroxy group before it is halogenated in the aforementioned manner to produce the compound of formula V-C. Hydrolysis is carried out in the same manner as described in connection with the compound of formula XVII where R$_9$ is an ether protecting group.

The compound of formula IV where R" is —COOH, is a known compound. The compound of formula IV where R is

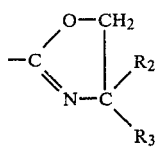

can be prepared by reacting the compound of IV where R" is —COOH with a compound of the formula:

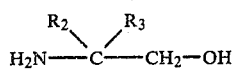 XXIII where $R_2$ and $R_3$ are as above.

This reaction is carried out by reacting the compound of formula IV where R" is —COOH with the compound of formula XXIII in an organic hydrocarbon solvent while removing water from the reaction medium. In general, this reaction is carried out at reflux while removing the water formed during this reaction. Any conventional method of removing water such as by azeotropic distillation can be utilized in this reaction. In carrying out this reaction, any conventional inert hydrocarbon solvent such as xylene, toluene, benzene, etc. can be utilized. In like manner, the compound of formula IV-A can be produced from a compound of formula:

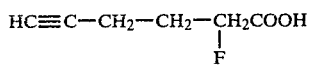 IV-D by reacting the compound of formula IV-D with the compound of formula XXIII. This reaction is carried out in the same manner as described in connection with the reaction of the compound of formula IV where R" is COOH with the compound of formula XXIII.

The compound of formula IV-D is prepared from a compound of formula

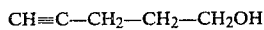 XXV via the following intermediates:

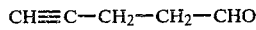 XXVI

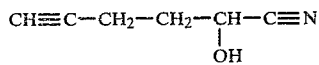 XXVII

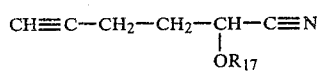 XXVIII

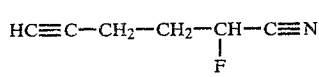 XXIX where —$OR_{17}$ is a leaving group.

The compound of formula XXV is converted to the compound of formula XXVI by oxidation. Any conventional oxidizing agent used for converting alcohols to aldehydes can be used in this reaction. The preferred oxidizing agent for use in this reaction is pyridinium chlorochromate. The compound of formula XXVI can be converted to the compound of formula XXVII by conventional procedures for a cyanohydration reaction such as by treating the compound of formula XXVI with an alkali metal cyanide such as potassium or sodium cyanide. Generally this reaction is carried out at room temperature and atmospheric pressure. If desired, higher or lower temperatures can be utilized. Furthermore, this reaction is generally carried out in an aqueous medium.

The compound of formula XXVII is converted to the compound of formula XXVII by converting the hydrogen on the hydroxy group in the compound of formula XXVII to a leaving group. Any conventional leaving group can be utilized. Among the preferred leaving groups are tosyloxy and mesyloxy with mesyloxy being especially preferred. Any conventional method of converting the hydroxy group to a mesyloxy or tosyloxy substituent can be utilized in converting the compound of formula XXVII to the compound of formula XXVIII. The compound of formula XXVIII is converted to the compound of formula XXIX by treating the compound of formula XXVIII with an alkali metal fluoride. In carrying out this reaction, temperatures of from 50° C. to 150° C. are utilized. Generally, this reaction is carried out in a high boiling organic solvent, i.e. an organic solvent boiling at 50° C. or greater. Among the preferred solvents that can be utilized are diethylene glycol, pentane, benzene, toluene, and dimethyl acetamide. The compound of formula XXIX is converted to the compound of formula IV-D by hydrolysis. Any conventional method of basic hydrolysis such as by treatment with an aqueous base such as potassium or sodium hydroxide can be utilized in carrying out this reaction.

The compound of formula IV-D can also be prepared by alkylating a compound of the formula:

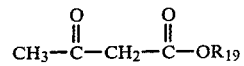 XXX with a substituted alkyl halide of the formula:

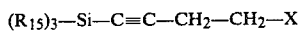 XXXI wherein $R_{15}$ and $R_{19}$ are lower alkyl; X is as above, to produce a compound of the formula:

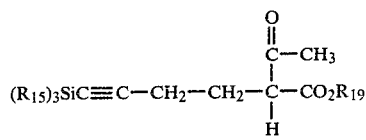 XXXII

This alkylation reaction is carried out by first treating the compound of formula XXX with an alkali metal base such as sodium hydride in an inert organic solvent to form the salt of the compound of formula XXX and then adding the compound of formula XXXI to the reaction mixture containing this salt. In carrying out this reaction, any conventional base can be utilized. Among the preferred bases are the alkali metal hydrides and the alkali metal lower alkoxides. In carrying out the alkylation reaction, both steps can be performed in the presence of an inert organic solvent. Any conventional inert organic solvent can be utilized. Among the preferred solvents are the ether solvents such as tetrahydrofuran, diethyl ether, as well as other solvents such as acetamide, dioxane, etc. While both the addition of the base and the subsequent reaction with the compound of formula XXXI can be carried out at room temperatures, it is generally preferred to carry out the subsequent reaction at higher temperatures, i.e. 40° to 100° C. Therefore, in accordance with the preferred embodiment of the invention, the compound of formula XXX is first treated with the base at room temperature in a low boiling ether solvent such as tetrahydrofuran. The resulting salt of the compound of formula XXX can, if desired, be isolated and reacted with the compound of formula XXXI at reflux, in a higher boiling inert organic solvent such as acetonitrile.

The compound of formula XXXII is converted to the compound of formula IV-D via the following intermediates:

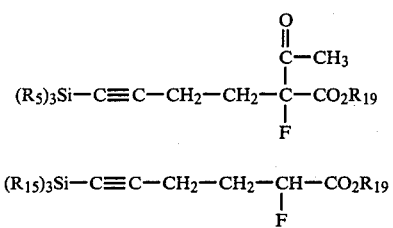

wherein $R_{15}$ and $R_{19}$ are as above.

The compound of formula XXXII is converted to the compound of formula XXXIII by first treating the compound of formula XXXII with a base such as the alkali metal hydrides or alkali metal hydroxides and then reacting the basic salt thus formed with a fluorinating agent such as perchloryl fluoride. This reaction is preferably carried out under an inert gaseous atmosphere such as argon. This reaction produces the compound of formulae XXXIII and XXXIV in admixture. This mixture can, if desired, be separated by conventional means such as chromatography. In carrying out the reaction whereby the compound of formula XXXII is converted to the compound of formula XXXIII and XXXIV, both the formation of the salt and the treatment with a fluorinating agent can be carried out in an inert organic solvent. Any conventional inert organic solvent can be utilized in carrying out these reactions. Among the preferred solvents are the hydrocarbon solvents such as toluene, benzene, etc. In carrying out the reaction, any conventional fluorinating agent, such as perchloryl fluoride, can be utilized. The reaction with the perchloryl fluoride or other conventional fluorinating agents is generally carried out at very low temperatures, −30° to 0° C. On the other hand, formation of the salt of the compound of formula XXXII is carried out at room temperature. In fact, any temperature of from 0°–50° C. can be utilized in forming this salt.

The compound of formula XXXIV can be converted to the compound of formula IV-D by hydrolysis in the presence of an aqueous alkali metal hydroxy such as sodium hydroxide. In general, any of the conditions conventional in hydrolysis with an alkali metal aqueous base can be utilized in carrying out this conversion. On the other hand, the compound of formula XXXIII can be hydrolyzed by first treating the compound of formula XXXIII with an alkali metal lower alkoxide in an inert organic solvent to convert the compound of formula XXXIII to the compound of formula XXXIV and thereafter hydrolyzing the compound of formula XXXIV with an aqueous alkali metal hydroxide to convert the compound of formula XXXIV with the compound of formula IV-D. The treatment with an alkali metal lower alkoxide can be carried out in the conventional manner utilizing an inert organic solvent, such as the lower alkanol solvents, particularly methanol ethanol, isopropanol, etc.

On the other hand, the mixture containing the compounds of formulae XXXIII and XXXIV need not be separated, but can be converted to the compound of formula IV-D by first treatment with an aqueous alkali metal alkoxide and then with an aqueous alkali metal lower hydroxide in the aforementioned manner.

The compound of formula I where R is —COOR$_{20}$ and R$_{20}$ is lower alkyl can be prepared from the corresponding compound of formula I where R is —COOH or

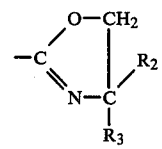

by esterification with a lower alkanol in the presence of a strong acid. Any conventional method of esterification can be utilized to carry out this reaction.

The compound of formula II can be prepared by reacting a compound of the formula

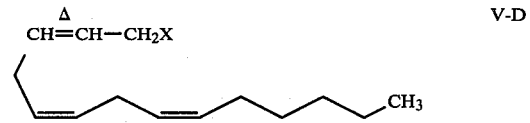

with a compound of the formula IV-A in the same manner as described hereinbefore in connection with the reaction of a compound V with the compound of the formula IV. This reaction produces a compound of the formula:

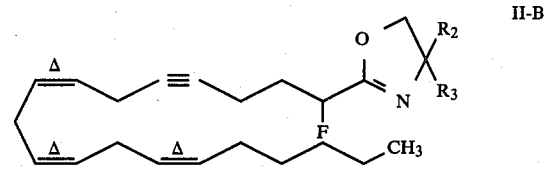

This compound can be hydrolyzed by treatment with an aqueous mineral acid as described in the conversion of a compound of formula I-B to I-C to produce the compound of the formula:

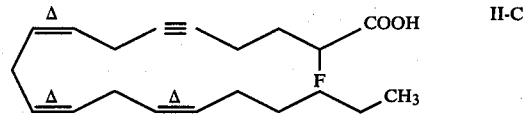

wherein Δ is as above.

The compound of formula II-C can be esterified with a lower alkanol in the manner described hereinbefore in connection with the esterification of a compound of formula I where R is COOH, to produce a compound of the formula:

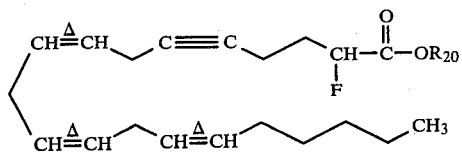

where $R_{20}$ is lower alkyl and $\Delta$ is as above. In the compounds of formula II, the double bonds have this cis configuration.

The compounds of formulae I and II where R is —COOH can be converted to their salts by conventional salt formation. Any conventional means of converting a free acid into a salt can be utilized in forming pharmaceutically acceptable basic salts of compounds of the formula I and II.

In all of the reactions described above which involve a compound containing a triple bond in either a reactant or a product, it is generally preferred to carry out this reaction under an inert gaseous atmosphere. Any conventional inert gas such as those mentioned hereinbefore can be utilized in carrying out these reactions involving a compound containing a triple bond as a reactant or as a product.

The invention is further illustrated by the following examples. In the examples, all temperatures are in degrees Centigrade. Ether, as utilized in these examples, refers to diethyl ether. The term "mm" refers to millimeters of mercury. Unless specified, all percents are percents by weight. In the Examples, "THF" designates tetrahydrofuran.

EXAMPLE 1

4-Pentyn-1-al

A mixture of 4-pentyn-1-ol(13.5 g, 16.05 mmol), pyridinium chlorochromate (51.9 g, 24.07 mmol), and sodium acetate (4.34 g, 5.29 mmol) in $CH_2Cl_2$ (200 ml) was stirred at 25° C. for 2.5 h. Ether was added and the mixture was filtered over about 50 g of celite and washed well with ether. After evaporation of ether on a rotary evaporator at 30° C./>100 mmHg, the resulting crude material was distilled to give 7.3 g (55%) of 4-pentyn-1-al as a colorless liquid, bp 65°–68° C./65 mm (Lit. bp 70°/50 mmHg).

EXAMPLE 2

2[(Methylsulfonyl)oxy]-5-hexynenitrile

A solution of sodium bisulfite (8.62 g, 82.8 mmol) in 20 ml of water was added at 0° C., to a mixture of 4-pentyn-1-al (6.8 g, 82.8 mmol) in 10 ml of water. The reaction mixture was stirred at 0° C. for ½ hr. A solution of sodium cyanide (4.05 g, 82.8 mmol) in 30 ml of water was then added portionwise and the mixture was further stirred at 0° C. for 1.0 h. It was extracted three times with ether. The combined ether extracts were washed with brine, dried over $Na_2SO_4$, and filtered. The ether was concentrated at 35° C./80–100 mm to give 8.07 g of 2-hydroxy-5-hexynenitrile as a colorless liquid which was used directly for the next step described below.

A mixture of 2-hydroxy-5-hexynenitrile (8.0 g, 73.3 mmol) and dry triethylamine (10.1 g, 0.1 mol) in 50 ml of dry $CH_2Cl_2$ was treated with a solution of methanesulfonyl chloride (10.3 g, 90 mmol) in 50 ml of $CH_2Cl_2$, at 0° C. for 1½ h. The reaction mixture was diluted with $CH_2Cl_2$, washed twice with cold 1.0 N $H_2SO_4$, twice with water, and dried over $MgSO_4$. The filtered $CH_2Cl_2$ solution was concentrated at 40° C./30 mm to give 12 g of pale yellow liquid. Purification of this material on 220 g of silica gel and eluted with ether-petroleum ether (1:1 parts by volume) gave 8.7 g (56% by weight yield from pentynal) of 2-[(methylsulfonyl)]-5-hexynenitrile as a colorless liquid.

EXAMPLE 3

2-Fluoro-5-Hexynoic Acid

A mixture of 2-[(methylsulfonyl)oxy]-5-hexynenitrile (7.7 g, 41.1 mmol) and dry potassium fluoride (3.57 g, 61.4 mmol) in 10 ml of dry diethylene glycol was heated with vigorous stirring, at 135° C. under argon for 2 h. The resulting black reaction mixture was taken into 50 ml of water and extracted with ether (3×25 ml). The combined ether extracts were washed with water and then treated with a solution of potassium hydroxide (2.3 g, 61.4 mmol) in 15 ml of water. The resulting mixture was heated with stirring, at 65° C. (bath) for 2.0 h. The ether was distilled off at one atmosphere, and the aqueous solution was cooled to about 25° C., diluted with 50 ml of ice-water, and extracted with ether (3×50 ml). The ether extracts were combined and extracted with 2×50 ml in NaOH solution. The combined NaOH solution was cooled to 0° C. and then acidified to pH 2.5 with cold 3 N $H_2SO_4$ solution. The resulting acidic aqueous phase was extracted with three times ether. The ether extracts were combined, washed with water, and dried ($MgSO_4$). Concentration of ether at 40° C./~ ±mm, and evaporative distillation of the resulting crude product at 130°/10 mmHg afforded 1.75 g (33% by weight yield) of 2-fluoro-5-hexynoic acid as a colorless liquid which solidified on cooling to a temperature of −10° C. to −20° C. as a white solid.

EXAMPLE 4

2-(1-Fluoro-4-pentynyl)-4,5-dihydro-4,4-dimethyloxazole

A mixture of 2-fluoro-5-hexynoic acid (3.0 g, 23.05 mmol) and 2-amino-2-methyl-1-propanol (2.05 g, 23.05 mmol) in 150 ml of dry xylene was refluxed for 16 h. The water formed during the reaction was removed by Linde 3A molecular sieves (15 g) contained in a continuous extractor. The xylene was then distilled off at atmospheric pressure, and the resulting pot material was taken into ether (100 ml). The ethereal solution was washed with saturated sodium bicarbonate solution, water, and dried over $MgSO_4$. Evaporation of ether at 35° C./~35 mm, and distillation of the resulting crude product gave 2.4 g (57%) of 2-(1-fluoro-4-pentynyl)-4,5-dihydro-4,4-dimethyloxazole as a colorless liquid, bp 62°–66° C./0.6 mmHg.

EXAMPLE 5

2-(1-Fluorononadec-13(Z)-en-4,7-diynyl)-4,5-dihydro-4,4-dimethyloxazole

A solution of ethyl magnesium bromide in THF (0.98 ml, 1.86 N) was added dropwise at 25° C., under argon, to a stirred solution of 2-(1-fluoro-4-pentynyl)-4,5-dihydro-4,4-dimethyloxazole (348 mg, 1.9 mmol) in THF (1 ml). The resulting reaction mixture was stirred at 25° C. under argon for 2.0 h. Copper (I) cyanide (18 mg, 0.2 mmol) was added and the mixture was stirred for ¼ h. A solution of (Z)-1-bromo-8-tetradecen-2-yne (500 mg, 1.84 mmol) in dry THF (1 ml) was then added dropwise and the resulting reaction mixture was stirred at 25° C. for 2 h, and was further refluxed for 3 h under argon.

The mixture was cooled in an ice bath, diluted with water (100 ml), and extracted three times with ether. The combined ether extracts were washed with water, dried over MgSO$_4$, filtered, and concentrated at 35° C./~35 mm. The crude oily product was purified by flash chromatography on silica gel (60 g) and eluted with ethyl acetate-petroleum ether (1:4 parts by volume) to yield 311 mg (45% by weight yield) of 2-(1-fluorononadec-13(Z)en-4,7-diynyl)-4,5-dihydro-4,4-dimethyloxazole as a colorless oil.

EXAMPLE 6

(Z)-2-Fluoro-1,4-Eicosene-5,8-diynoic acid

A suspension of 2-(1-fluorononadec-13-en-4,7-diynyl)-4,5-dihydro-4,4-dimethyloxazole (86 mg) in 3 ml of 3 N HCl was refluxed with stirring under argon for 15 min. It was cooled to about 23° C., diluted with 3 ml of water, and extracted three times with ether. The ether extracts were combined, washed with brine, and dried over MgSO$_4$. Concentration of ether at 35° C./35 mmHg gave the crude acid which was purified by flash chromatography on silica gel (8 g, 230-400 mesh). Elution with HOAc-CH$_3$OH—CHCl$_3$ under nitrogen afforded 49 mg (66% yield by weight) of (Z)-2-fluoro-14-eicosene-5,8-diynoic acid as a colorless oil.

EXAMPLE 7

2-[(Z)-13-Nonadecen-4,7-diynyl]-4,5-dihydro-4,4-dimethyloxazole

In a similar manner as described above in Example 5 for the preparation of 2-[1-fluorononadec-13(Z)-en-4,7-diynyl)]-4,5-dihydro-4,4-dimethyloxazole, 2-[(Z)-13-nonadecen-4,7-diynyl]-4,5-dihydro-4,4-dimethyloxazole was synthesized from (Z)-1-bromo-8-tetradecen-2-yne and 2-(4-pentynyl)-4,5-dihydro-4,4-dimethyloxazole.

EXAMPLE 8

Preparation of 2-Acetyl-6-(trimethylsilyl)-5-hexynoic acid ethyl ester

Ethyl aceteoacetate (11.6 g) was added dropwise to an ice-cooled suspension of sodium hydride (2.0 g) in tetrahydrofuran (150 ml) under a positive argon atmosphere After stirring for 30 minutes, the reaction mixture was allowed to stand until the solids had settled. The clear solution was removed via a transfer needle and then condensed by rotary evaporation to yield an off-white solid. This material was mixed with acetonitrile (150 ml) and heated to reflux under a postive argon atmosphere as 4-iodo-1-butynyltrimethylsilane (16.0 g) was added. The reaction mixture was heated to reflux for 21 hours. The volatiles were removed by rotary evaporation and the residual material partitioned between hexane and dilute hydrochloric acid. The hexane layer was washed with sat. sodium bicarbonate solution, dried (MgSO$_4$) and condensed by rotary evaporation to yield an oil. This material was vacuum distilled to give 8.24 g of 2-acetyl-6-(trimethylsilyl)-5-hexynoic acid ethyl ester; bp 97°–101°/0.005 mmHg.

EXAMPLE 9

Preparation of 2-Acetyl-2-Fluoro-6-(Trimethylsilyl)-5-hexynoic Acid ethyl ester and 2-Fluoro-6-(trimethylsilyl)-5-hexynoic acid ethyl ester 2-acetyl-6-(trimethylsilyl)-5-hexynoic acid ethyl ester (7.1 g) was added to a suspension of sodium hydride (1.0 g) in toluene under a positive argon atmosphere. After stirring for 1 hour, the reaction mixture was cooled to −10° and a mixture of perchloryl fluoride and argon gases was bubbled through the reaction mixture at such a rate that the internal temperature never exceeded 0° C. The perchloryl fluoride addition was discontinued when it ceased to be exothermic. Argon was bubbled through the mixture as it was allowed to warm to room temperature. The reaction mixture was partitioned between hexane and water and the organic phase was dried (MgSO$_4$) and condensed by rotary evaporation to give an oil. The components of the oil were separated by silica gel chromatography using 30% ethyl acetate/hexane as the eluant to give 5.9 g of 2-acetyl-2-fluoro-6-(trimethylsilyl)-5-hexynoic acid ethyl ester. There was also obtained 0.25 g of 2-fluoro-6-(trimethylsilyl)-5-hexynoic acid ethyl ester.

EXAMPLE 10

Preparation of 2-Fluoro-5-Hexynoic Acid

To a solution of 2-acetyl-2-fluoro-6-(trimethylsilyl)-5-hexynoic acid ethyl ester (6.63 g) in ethanol (20 ml) was added 27 ml of 2.65 M sodium ethoxide/ethanol. After 18 hours, 7 ml of 4 N sodium hydroxide was added. After 6 hours, the solvent was removed by rotary evaporation and the residual materials partitioned between ethyl ether and dilute hydrochloric acid. The organic layer was dried (MgSO$_4$) and the solvent removed by rotary evaporation to give an oil which was vacuum distilled to yield 3.2 g of 2-fluoro-5-hexynoic acid; b.p. 118°/14 mmHg.

EXAMPLE 11

(Z,Z)-2,5-Undecadien-1-ol 2,5-undecadiyn-1-ol (1.5 g) in absolute ethanol (15 ml) was reduced with Lindlar catalyst (0.33 g) in the presence of quinoline (0.1 ml) at 25° C., 1 atm., for 7 h. The uptake of hydrogen stopped at 420 ml (theoretical 428 ml). The solution was filtered, and the solvent was evaporated to give 1.5 g of crude product which was then purified by column chromatography on silica gel (50 g). Elution with ether-petroleum ether (1:4 parts by volume) gave 1.07 g of (Z,Z)-2,5-undecadien-1-ol as an oil.

EXAMPLE 12

(Z,Z)-1-Chloro-2,5-undecadiene

A mixture of (Z,Z)-undecadien-1-ol (3.42 g, 20.4 mmol) and triphenylphosphine (7.5 g, 28.6 mmol) in dry CCl$_4$ (25 ml) was refluxed with stirring for 9 h. The reaction mixture was allowed to cool to 23° C., hexane (60 ml) was added, and stirring was continued for an additional 10 minutes. The precipitate of triphenylphosphine oxide was filtered and washed with hexane. The solvent was removed from the combined filtrate at 40° C./~30 mmHg. Evaporation distillation of the resulting residue at 125°–130° C./0.3 mmHg gave 3.5 g (92%) of (Z,Z)-1-chloro-2,5-undecadiene as a colorless liquid.

EXAMPLE 13

(Z,Z)-5,8-Tetradecadien-2-yn-1-ol

A solution of ethylmagnesium bromide in THF (10 ml) was prepared from magnesium (1.4 g, 57.7 mmol) and ethyl bromide (7.7 g, 71 mmol). Propargyl alcohol (1.53 g, 27.4 mmol) in dry THF (6 ml) was then added dropwise to the above ethylmagnesium bromide solution at 5° C. with vigorous stirring. The resulting viscous mixture was stirred at 23° C. under argon for twenty minutes. Cuprous chloride (0.14 g) was added and the reaction mixture was further stirred for twenty minutes. A solution of (Z,Z)-1-chloro-2,5-undecadiene (3.4 g, 18.2 mmol) in THF (2.0 ml) was then added dropwise to the above mentioned mixture over a period of twenty five minutes, at 20° C. The reaction mixture was stirred at 50° C. under argon for 18 h. The THF was removed at ~35° C. on a rotary evaporator and the resulting residue was treated with cold 1.5 N $H_2SO_4$ (150 ml). It was extracted with ether, washed with water, and dried over $Na_2SO_4$. Evaporation of ether at reduced pressure gave 3.7 g of light yellow oil which was chromtographed on 70 g of silica gel. Elution with ether-petroleum ether (1:3) gave 2.3 g (61%) of (Z,Z)-5,8-tetradecadien-2-yn-1-ol which was evaporatively distilled at 137°–140° C./0.3 mmHg as a colorless liquid.

EXAMPLE 14

(Z,Z)-1-Bromo-5,8-tetradecadien-2-yne

A solution of phosphorous tribromide (0.47 g, 1.73 mmol) in absolute ether (0.5 ml) was added dropwise during five minutes to a mixture of (Z,Z)-5,8-tetradecadien-2-yn-1-ol (1.03 g, 5 mmol), and dry pyridine (14 mg, 0.18 mmol) in 8 ml of absolute ether. The reaction mixture was heated under reflux for 2.5 h, cooled to 23° C., then poured onto ice-water. It was extracted three times with ether. The combined ether extracts were washed with dilute aqueous sodium bicarbonate solution, water, dried over $Na_2SO_4$ and concentrated in vacuo. Evaporative distillation of the crude product at 145°–148° C./0.15 mm afforded 1.1 g (80.5%) of (Z,Z)-1-bromo-5,8-tetradecadien-2-yne as a pale yellow oil.

EXAMPLE 15

(Z,Z)-11,14-Eicosadien-5,8-Diynoic Acid

A solution of 5-hexynoic acid (0.73 g, 6.5 mmol) in dry THF (2 ml) was added dropwise at 4° C., under argon, to a vigorously stirred mixture of ethylmagnesium bromide (prepared from 0.32 g, 13.2 mg-atom of magnesium, and 2.04 g, 18.7 mmol of ethyl bromide) in 5 ml of dry THF. The reaction mixture was then stirred at 23° C. under argon for 1.5 h. Cuprous cyanide (40 mg, 0.45 mmol) was added and the mixture was further stirred for 10 min. A solution of (Z,Z)-1-bromo-5,8-tetradecadien-2-yne (0.58 g, 2.0 mmol) in 2 ml of dry THF was then added dropwise at 23° C. under argon. The resulting reaction mixture was stirred at 23° C. under argon for 20 h. It was poured into cold 2 N $H_2SO_4$ and extracted three times with ether. The combined ether extracts were extracted three times with 1 N $NH_4OH$ solution. Acidification of the combined ammonia hydroxide solution to pH 3, followed by isolation of the product by the usual ether extraction procedure gave 0.98 g of crude acidic product. Evaporative distillation of this material at 75°–84° C./0.15 mmHg gave 0.14 g of 5-hexynoic acid. The pot residue (0.81 g) was chromatographed on 40 g of silica gel (silica gel 60, 230–400 mesh) under a slight pressure of nitrogen. Elution with ether-petroleum ether (2:3 parts by volume) gave 0.33 g (55% yield based on bromide) of (Z,Z)-11,14-eicosadien-5,8-diynoic acid as a pale yellow oil.

EXAMPLE 16

(Z,Z)-11,14-Eicosadien-5,8-Diynoic Acid Methyl Ester

Treatment of (Z,Z)-11,14-eicosadien-5,8-diynoic acid with diazomethane in ether at 4° C. for 0.5 h gave the corresponding methyl ester as a pale yellow oil: bp 160°–175° C./0.01 mmHg (evaporative distillation).

EXAMPLE 17

(Z)-5-Undecen-1-ol

A mixture of n-hexyltriphenylphosphonium bromide (75 g, 0.175 mmol) and sodium bistrimethylsilylamide (31.5 g, 0.17 mol) in dry THF (400 ml) was stirred at 23° C. under argon for 3 h. To the resulting bright orange suspension, a solution of 5-hydroxypentanal (8.04 g, 78 mmol) in 25 ml of dry THF was added. The reaction mixture was stirred at 23° C. under argon for 3.0 h. The THF was evaporated at reduced pressure and the resulting residue was treated with 200 ml of water and extracted three times with ether. The combined ether extracts were washed with water, dried over anhydrous $Na_2SO_4$, and evaporated at reduced pressure to give 21.8 g of pale yellow oil after a quick chromatography on 400 g of silica gel using ether-petroleum ether (1:1 parts by volume) as eluent. Distillation of this material gave 11.4 g (80% by weight yield based on aldehyde) of (Z)-5-undecen-1-ol as a colorless liquid: bp 101°–102° C./15 mmHg.

EXAMPLE 18

(Z)-1-Bromo-5-Undecene

A solution of phosphorous tribromide (2.09 g, 7.8 mmol) in dry ether (2 ml) was added dropwise, at 25° C., to a mixture of (Z)-5-undecen-1-ol (4.24 g, 23.1 mmol), and pyridine (79 mg, 1 mmol) in 25 ml of dry ether. The resulting reaction mixture was heated under reflux with stirring under argon for 2 h. It was cooled to 23° C., poured onto water (100 ml), and extracted three times with ether. The ether extracts were combined, washed two times each with saturated aqueous sodium bicarbonate solution, water, and dried over anhydrous $Na_2SO_4$. Evaporation of ether to dryness at reduced pressure yielded 3.8 g of material. This was filtered over 35 g of silica gel and eluted with ether-petroleum ether (2:3 parts by volume). The fractions containing the desired product were combined and the solvent was evaporated at reduced pressure. The resulting residue was purified by evaporative distillation at 105°–110° C./0.2 mmHg to give 2.73 g (51% by weight yield) of (Z)-1-bromo-5-undecene as a colorless liquid.

EXAMPLE 19

1-(Tetrahydro-2-pyranoxy)-(Z)-8-tetradecen-2-yne

A solution of n-butyllithium (11.5 ml, 27.3 mmol) in hexane was added dropwise, under an argon atmosphere, over a period of 10 minutes to a solution of 1-(tetrahydro-2-pyranoxy)-2-propyne (3.83 g, 27.3 mmol) in 30 ml of dry THF, while the temperature of the reaction mixture was kept below 10° C. To the resulting yellow lithium acetylide solution, a solution of (Z)-1-bromo-5-undecene (6.07 g, 27.3 mmol) in 30 ml of dry hexamethylphosphoric triamide (HMPA) was added at 4° C. The reaction mixture was stirred at 23° C. under argon for 1.0 h, and then poured into ice-water (100 ml). It was extracted three times with ether. The combined ether extracts were washed with brine, dried over anhydrous Na$_2$SO$_4$, and evaporated at reduced pressure to give 8.0 g of product. This material was quickly filtered over 40 g of silica gel. Elution with ether-petroleum ether (2:3 parts by volume) gave 6.6 g (83% by weight yeild) of 1-(tetrahydro-2-pyranoxy)-(Z)-8-tetradecen-2-yne as a pale yellow oil, which was used directly for the next step described below.

EXAMPLE 20

(Z)-8-Tetradecen-2-yn-1-ol

A mixture of 1-(tetrahydro-2-pyranoxy)-(Z)-8-tetradecen-2-yne (6.2 g, 21.2 mmol) and p-toluenesulfonic acid (0.46 g) in 50 ml of methanol was stirred at 23° C. under argon for 1.0 h. Solid sodium carbonate (2 g) was added and the mixture was stirred for an additional fifteen minutes. It was filtered, washed with methanol, and concentrated to nearly dryness. The resulting oily residue was taken into ether, washed with water, and dried over anhydrous Na$_2$SO$_4$. Evaporation of ether in vacuo gave an oily material which was passed through a column of 35 g of silica gel and eluted with ether-petroleum ether (1:1 parts by volume) to yield 4.2 g of pale yellow oil. Evaporative distillation of this material at 90° C./0.2 mmHg afforded 3.8 g (85% by weight yield) of (Z)-8-tetradecen-2-yn-1-ol as a colorless oil.

EXAMPLE 21

(Z)-1-Bromo-8-tetradecen-2-yne

By the procedure of example 14, 3.82 g (18.34 mmol) of (Z)-8-tetradecen-2-yn-1-ol, 72 mg of dry pyridine, and 1.66 g (6.12 mmol) of phosphorous tribromide were reacted in 20 ml of ether under reflux for 2.0 h. It was worked up as described in example 14 to give 3.83 g of crude product. It was purified by evaporative distillation at 105° C.–120° C./0.25 mm to yield 3.64 g (73% by weight yield) of (Z)-1-bromo-8-tetradecen-2-yne as a colorless oil.

EXAMPLE 22

(Z)-14-Eicosen-5,8-diynoic acid

By the procedure of example 15, the di-Grignard complex of 5-hexynoic acid (213 mg, 1.9 mmol) was prepared from magnesium (93 mg, 4.0 mmol) and ethyl bromide (458 mg, 4.2 mmol) in 3 ml of dry THF. To this mixture cuprous cyanide (18 mg, 0.2 mmol) was added and stirring was continued for 10 min. A solution of (Z)-1-bromo-8-tetradecen-2-yne (540 mg, 2.0 mmol) in THF (2 ml) was then added dropwise. The reaction mixture was stirred at 23° C. under argon for 18 h, and was further heated under reflux for 5 h. Work up of the reaction mixture and purification of the crude product as described in example 15 gave 326 mg of (Z)-14-eicosen-5,8-diynoic acid as a pale yellow oil.

EXAMPLE 23

(Z)-2-Undecen-1-ol

A mixture of 2-undecyl-1-ol (15 g), quinoline (0.6 ml), and 9 g of Lindlar catalyst was hydrogenated at 23° C., 1 atm until the uptake of hydrogen was complete. The catalyst was filtered off and washed with hexane. The hexane solution was washed with 1 N HCl solution, brine, and dried over anhydrous Na$_2$SO$_4$. Concentration of solvent in vacuo and distillation of the resulting residue gave 13.3 g of (Z)-2-undecen-1-ol as a colorless oil: bp 77°–80° C./0.1 mmHg.

EXAMPLE 24

(Z)-1-Chloro-2-undecene

By the procedure of example 12, (Z)-2-undecen-1-ol (13 g), 27.8 g of triphenylphosphine in 100 ml of dry CCl$_4$ were reacted under reflux for 6.5 h. Workup as described before as in example 12 gave 12.3 g of (Z)-1-chloro-2-undecene as a colorless oil: bp 65°–66° C./0.2 mmHg.

EXAMPLE 25

(Z)-5-Tetradecen-2-yn-1-ol

By the procedure of example 13, (Z)-1-chloro-2-undecene (4.0 g, 21 mmol), the Grignard complex of propargyl alcohol (prepared from 35 mmol of propargyl alcohol and 70 mmol of ethylmagnesium bromide in 35 ml of dry THF), and 252 mg of CuCl were allowed to react at 50° C. for 20 h. under argon. Workup of the reaction mixture and purification of the crude product as described before in example 13 gave 2.54 g (58% by weight yield) of (Z)-5-tetradecen-2-yn-1-ol as a colorless oil, bp 102°–127° C./0.25 mmHg (evaporative distillation).

EXAMPLE 26

By the same procedure of example 14, (Z)-5-tetradecen-2-yn-1-ol was converted to (Z)-1-bromo-5-tetradecen-2-yne.

EXAMPLE 27

(Z)-11-Eicosen-5,8-diynoic acid

By the same procedure of example 22, (Z)-1-bromo-5-tetradecen-2-yne, and the Grignard complex of 5-hexynoic acid gave (Z)-11-eiconsen-5,8-diynoic acid.

EXAMPLE 28

2-[1-Fluorononadeca-7(Z),10(Z),13(Z)-trien-4-ynyl]-4,5-dihydro-4,4-dimethyloxazole A solution of 2-(1-fluoro-4-pentynyl)-4,5-dihydro-4,4-dimethyloxazole (1.09 g, 6.0 mmol) in 2 ml of dry THF was treated, dropwise, at 0° C., under argon, with 2.26 ml (2.65 N in THF) of ethylmagnesium bromide. The resulting mixture was stirred at 25° C. under argon for 2 h. Copper I cyanide (54 mg) was then added, and the mixture was stirred at 25° C. for 15 min. A solution of 1-chloro-2(Z),5(Z),8(Z)-tetradecatriene (544 mg, 2.4 mmol) in a small amount of dry THF was added. The reaction mixture was stirred at 25° C. for 2 h, and then at 40° C. for 10 h under argon. Water was added and the mixture was extracted with ether. The ether extracts were combined, washed with water, dried over anhydrous MgSO$_4$, filtered, and concentrated in vacuo. The crude product was purified by flash column chromatography on 120 g of silica gel. Elution with CH$_2$Cl$_2$-ether (19:1) gave 171 mg of 2-[1-fluorononadeca-7(Z),10(Z),13(Z)-trien-4-ynyl]-4,5-dihydro-4,4-dimethyloxazole as a colorless oil.

EXAMPLE 29

2-Fluoro-8(Z),11(Z),14(Z)-eicosatrien-5-ynoic acid

2-[1-fluorononadeca-7(Z),10(Z),13(Z)-trien-4-ynyl]-4,5-dihydro-4,4-dimethyloxazole was hydrolyzed in refluxing 3 N HCl for 15 min. as described in Example 6, to give 2-fluoro-8(Z),11(Z),14(Z)-eicosatrien-5-ynoic acid as a colorless oil.

In Examples 30–33, the compounds of this invention were tested against 5,8,11,14-eicosatetraynoic acid and 9,12-octadecdiynoic acid. The compound 5,8,11,14-eicosatetraynoic acid is standard potent inhibitor of SRS-A synthesis as well as of $\Delta^{12}$-lipoxygenase and prostaglandin endoperoxide synthase. On the other hand, the 9,12-octadecadiynoic acid is also a potent standard inhibitor of SRS-A synthesis and prostaglandin endoperoxide synthase while not being an inhibitor of $\Delta^{12}$lipoxygenase.

The compounds tested were as follows:

Compound 3. (Z,Z)-11,14-eicosadien-5,8-diynoic acid.
Compound 4. (Z,Z)-11,14-eicosadien-5,8-diynoic acid methyl ester.
Compound 5. (Z)-11-eicosen-5,8-diynoic acid.
Compound 6. (Z)-14-eicosen-5,8-diynoic acid
Compound 7. 2[(Z)-13-nonadecen-4,7-diynyl]-4,5-dihydro-4,4-dimethyloxazole.
Compound 8. 2-(1-fluorononadec-13(Z)-en-4,7-diynyl)-4,5-dihydro-4,4-dimethyloxazole.

EXAMPLE 30

Inhibition in the In Vitro Synthesis of SRS-A in Rat Peritoneal Cells

To study the effect of drugs on SRS-A synthesis in rat peritoneal cells, these cells (including mast cells, monocytes, eosinophils and neutrophils) were isolated from male Spague-Dawley rats (Charles River Laboratories) weighing 180–220 g by the lavage procedure described by Herzig, D. J. and Kusner, E. J., Journal of Pharmacology and Experimental Therapeutics, 194, 457–462 (1975) with the exception that Hanks balanced salt solution used in these experiments was adjusted to pH 6.9 with 5% (V/V) of 0.1 M aqueous phosphate buffer and contained 50 mg/ml sodium heparin. After removal from the peritoneal cavity of rats, the cells were subsequently isolated by centrifugation at 400×gravity for 10 minutes at 4° C. and resuspended to a concentration of about 2,000,000 cells per ml in Hanks buffer.

Samples for evaluation were prepared by adding various concentrations of test drugs to 2 ml aliquots of the resuspensed cells in Hanks buffer. The 2 ml samples used for control contained 2 ml aliquots of resuspended cells in Hanks buffer without drugs. All of the above samples (2 ml final volume) were preincubated at 37° C. for 10 minutes in the presence of varying concentrations of test drug prior to challenge with $5 \times 10^{-7}$ M ionophore A23107. This ionophore is disclosed in Burka and Flower, Br. J. Pharmacology 65:35–41 (1979). Antibiotic A23187 was used as a probe for the study of calcium and magnesium function in biological systems. After ionophore challenge, SRS-A was synthesized in the samples by the cells for 10 minutes (at 37° C.) after which this synthesis was terminated by placing the samples in a boiling water bath for 10 minutes followed by centrifugation at 2,000×g (10 minutes) at 4° C. to remove coagulated protein and cellular debris. The SRS-A present in the resulting supernatants was quantitated by a bioassay using a guinea pig ileum as described in Orange, and Austen, Adv. Immunol. 10:105–144 144 (1969). For this bioassay, a 1.5 cm segment of ileum was removed from animals weighing 300 to 400 g and suspended in an organ bath containing 10 ml of Tyrodes solution with $10^{-6}$ M atropine sulfate and $10^{-6}$ M pyrilamine maleate. The bath was maintained at 37° C. and aereated with a mixture of 95% $O_2$ and 5%$CO_2$. The concentration of SRS-A in the experimental samples was determined by a comparison of the isotonic contraction responses elicited by the samples with those obtained with varying amounts of an SRS-A standard solution prepared from chopped guinea pig lung as disclosed in Hitchcock, M. J. Pharmacol. Exp. Ther. 207: 630–640 (1978) and quantituted by the procedures of Orange, R. R. and Austen, K. F. Adv. Immunol. 10:105–144 (1969) against histamine (1 unit of SRS-A being that amount which gives a contractile response similar to that of 5 μg of histamine). In the absence of drug, the ionophore A23187-induced SRS-A synthesis varied between 40 to 50 units of SRS-A per $10^6$ cells. In the presence of increasing concentrations of test drug, there was a concentration-related decrease in SRS-A synthesis.

The mean percent inhibition=

$$\frac{\text{difference of units of SRS-A in test sample}}{\text{units of SRS-A in control}} \times 100$$

at each concentration of the various test drugs was calculated. The concentration of test drug which inhibits the synthesis of SRS-A by 50% ($IC_{50}$) was determined for each test drug from a plot of the mean percent inhibition versus the log of drug concentration. Both the % inhibition at 10 μM and the $IC_{50}$ are given in the following table. The difference of units of SRS-A in the test sample used in the fraction given above was obtained by substracting from the units of SRS-A in the control from the actual measurement of the units of SRS-A in the sample.

EXAMPLE 31

Assays for $\Delta^{12}$-Lipoxygenase $\Delta^{12}$-lipoxygenase activity was measured by following the conversion of $^{14}C$-arachidonic acid (AA) to $^{14}C$-12-hydroxy-5,8,10,14-eicosatetraenoic acid (12-HETE) using human platelets as the enzyme source. Washed human platelets from approximately 2000 ml of blood were suspended in 50 ml of phosphate buffered saline (PBS) and then lysed by freezing and thawing (3 times). The platelet lysate was homogenized using a glass-teflon homogenizer and then particulate material was sedimented by centifugation at 100,000×g for 1 hr and the sediment was discarded. The supernatant was made 50% by weight saturated with respect to $(NH_4)_2SO_4$ by adding solid ammonium sulfate. The resultant suspension was allowed to stand at 0° overnight. The precipitate was collected by centrifugation and was dissolved in approximately 25 ml of PBS. This solution was the enzyme solution utilized to catalyze the conversion of AA to 12 HETE.

In order to test the compounds, separate incubation tubes for each of the compounds and for concentrations of these compounds were prepared in an ice bath. These tubes each contained 140 μl of PBS containing 1.78 mM glutathione, 10 μl of test drug in ethanol, 50 μl of platelet supernatant, and 50 μl of $^{14}C$-AA. Incubation tubes used as the enzyme control did not contain any test compound but rather contained 10 μl of ethanol. Incubation tubes were prepared containing only buffer ethanol and $^{14}c$-AA were included as substrate controls. The final concentration of AA added as its ammonium salt in PBS, in each of the incubation tubes was 3–4 μM. Sufficient enzyme solution prepared as above was added so that, under the conditions of the assay, approximately 80–90% by weight of the $^{14}C$-AA was converted to 12-HETE, as determined by prior controls.

The tubes were incubated at 37° for 2 min, the reaction was stopped by the addition, while mixing on a mixer, of 2 ml of diethyl ether and 50 μl of 1 M citric acid. The ether in the presence of citric acid extracted 12-HETE and AA from enzyme in the reaction medium in each of the samples. The ether extract was evaporated to dryness under nitrogen and then the residue was dissolved in 50 μl of chloroform:methanol (2:1 parts by volume). The dissolved residue containing 12-HETE and AA was applied, as rapidly as possible, to a glass fiber sheet impregnated with silica gel and then the chromatogram was developed using isooctane:methylethylketone:acetic acid (100:9:1 parts by volume) as solvent. Radioactive products and unconverted $^{14}$C-AA were located using a thin-layer chromatography scanner. The appropriate regions of the chromatogram were cut out, then the radioactivity quantitated using a liquid scintillation counter. The amount of $^{14}$C-AA converted to product is used as a measure of $\Delta^{12}$-lipoxygenase activity.

The mean percent inhibition was calculated by multiplying 100 times the following fraction:

$$\frac{\text{Amount of }^{14}\text{C-AA in test sample} - \text{Amount }^{14}\text{C-AA in enzyme control}}{\text{Amount of }^{14}\text{C-AA in substrate control} - \text{Amount of }^{14}\text{C-AA in enzyme control}}$$

at each concentration of the various test drugs was calculated. The concentration of test drug which inhibits the conversion of 14-AA to 12-HETE by 50% (IC$_{50}$) was determined for each test drug from a plot of the mean percent inhibition versus log of drug concentration. This result is given in the following table.

EXAMPLE 32

Prostaglandin Endoperoxidesynthase (PES)

The activity of PES was measured polarigraphically by following the disappearance of dissolved O$_2$ from incubation mixtures containing arachidonic acid (AA) as substrate and sheep seminal vesicular gland microsomes (SSVM) as the enzyme source. Fifty mg of an acetone powder of SSVM were suspended, using a glass teflon homogenizer, in 1 ml of 0.1 M tris. HCl (pH, 8.5) containing 0.67 mM phenol. This suspension of SSVM was incubated at room temperature in the presence of phenol to maximumly activate the PES and then the suspension was kept at 0°.

Samples in a separate reaction vessel were each prepared by adding tris-phenol buffer (2.8 ml), 0.05 ml of the SSVM suspension, and a maximum of 0.12 ml of ethanol containing various concentrations of the test drug. The controls were prepared in the same manner except that the ethanol added did not contain any test drug. Reaction vessels were then allowed to reach temperature equilibrium. An oxygen electrode is inserted into the vessel and then 24 μl of 4.1 mM AA are injected into the sealed vessel through a port on the side of the electrode. The final concentration of AA is 33 μM. Oxygen uptake is recorded and the initial rate of oxygen uptake used as a measure of PES activity. Each of the test compounds were tested initially at a high concentration (1 mM) and then, if required, dilutions are made.

The mean percent inhibition was obtained for each concentration of the various test drugs by expressing as a percent the number obtained by dividing the difference of the oxygen uptake of the test sample by the oxygen uptake of the control. The concentration of test drug which inhibits the synthesis of PES by 50% (IC$_{50}$) which is given in the following table was determined for each test drug from a plot of mean percent inhibition verses drug concentration. The difference of the oxygen uptake of test sample was obtained by subtracting from the oxygen uptake of the control, the oxygen uptake of the test sample.

The results of the tests of Examples 30 through 32 with respect to the compounds of this invention are given in the foregoing Table. As seen from this Table, the compounds of this invention, i.e. compounds 3 through 5, are effective inhibitors of SRS-A synthesis.

Certain of these compounds, e.g. test compounds 3 through 5 of Table were only moderately effective inhibitors of $\Delta^{12}$-lipoxygenase whereas compounds 6 through 8 were not effective either in inhibiting the activity of other body factors such as $\Delta^{12}$-lipoxygenase and prostaglandin endoperoxide. These results show that the compounds of this invention are relatively selective in inhibiting SRS-A synthesis without substantially inhibiting other enzymes when compared to standard SRS-A synthesis inhibitors, i.e. the compounds 1 and 2.

TABLE

| TEST COMPOUNDS | SRS-A SYNTHESIS (Rat Peritoneal Cells) % Inhibition at 10 μM | SRS-A SYNTHESIS (Rat Peritoneal Cells) IC$_{50}$(μM) | $\Delta^{12}$-LIPOXYGENASE (Human Platelet) IC$_{50}$(μM) | PROSTAGLANDIN ENDO PEROXIDE SYNTHASE IC$_{50}$(μM) |
|---|---|---|---|---|
| 1. 5,8,11,14-Eicosatetraynoic Acid | 100 ± 0 (p < 0.001) | 3–4 | 0.05–0.1 | 5 |
| 2. 9,12-Octadecadiynoic Acid | 87 ± 1 (p < 0.001) | 3 | ≧100 | 0.1–1.0 |
| Compound 3. | 81 ± 6 (p < 0.01) | 4–5 | 10–100 | 10–100 |
| Compound 4. | 85 ± 8 (p < 0.001) | <10 | 10–100 | — |
| Compound 5. | 100 ± 0 (p < 0.001) | ~1–3 | 13 | >100 |
| Compound 6. | 100 ± 0 (p < 0.001) | ~1–3 | ~100 | >100 |
| Compound 7. | 86 ± 8 (p < 0.001) | <10 | ~100 | |
| Compound 8. | 88 ± 6 (p < 0.001) | <10 | >100 | |

EXAMPLE 33

Capsule Formulation of (Z,Z)-11,14-eicosadien-5,8-diynoic acid

| | | mg/capsule | | | | |
|---|---|---|---|---|---|---|
| Item | Ingredients | 0.1 | 0.5 | 5.0 | 10.0 | 25.0 |
| 1. | (Z,Z)-11,14-eicosadien-5,8-diynoic acid | 0.1 | 0.5 | 5.0 | 10.0 | 25.0 |
| 2. | Lactose | 183.9 | 183.5 | 179.0 | 218.0 | 257.0 |

-continued

| Item | Ingredients | mg/capsule | | | | |
|---|---|---|---|---|---|---|
| | | 0.1 | 0.5 | 5.0 | 10.0 | 25.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures
1. Mix Items 1–3 in a suitable mixer. Mill through a suitable mill.
2. Mix with Items 4 and 5 and fill on capsule machine.

EXAMPLE 34

Tablet Formulation (Wet Granulation) of (Z,Z)-11,14-eicosadien-5,8-diynoic acid

| Item | Ingredients | mg/capsule | | | | |
|---|---|---|---|---|---|---|
| | | 0.1 | 0.5 | 5.0 | 10.0 | 25.0 |
| 1. | (Z,Z)-11,14-eicosadien-5,8-diynoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure
1. Mix Items 1–5 in a suitable mixer, granulate with water. Dry, mill.
2. Mix with Item 5 and compress on a suitable press.

EXAMPLE 35

Tablet Formulation (Direct Compression) of (Z,Z)-11,14-eicosdaien-5,8-diynoic acid

| Item | Ingredients | mg/capsule | | | | |
|---|---|---|---|---|---|---|
| | | 0.1 | 0.5 | 5.0 | 10.0 | 25.0 |
| 1. | (Z,Z)-11,14-eicosadien-5,8-diynoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure
1. Mix Items 1–5 in a suitable mixer for 10–15 minutes.
2. Add magnesium stearate (Item 5) as a premix and mix for 4 minutes.
3. Compress on a suitable press.

EXAMPLE 36

Capsule Formulations of (Z,Z)-11,14-eicosadien-5,8-diynoic acid methyl ester

| Item | Ingredients | mg/capsule | | | | |
|---|---|---|---|---|---|---|
| | | 0.1 | 0.5 | 5.0 | 10.0 | 25.0 |
| 1. | (Z,Z)-11,14-eicosadien-5,8-diynoic acid methyl ester | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures
1. Mix Items 1–3 in a suitable mixer. Mill through a suitable mill.
2. Mix with Items 4 and 5 and fill on capsule machine.

EXAMPLE 37

Tablet Formulation (Direct Compression) of (Z,Z)-11,14-eicosadien-5,8-diynoic acid methyl ester

| Item | Ingredients | mg/tablet | | | | |
|---|---|---|---|---|---|---|
| | | 0.1 | 0.5 | 5.0 | 10.0 | 25.0 |
| 2. | (Z,Z)-11,14-eicosadien-5,8-diynoic acid methyl ester | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure
1. Mix Items 1–5 in a suitable mixer for 10–15 minutes.
2. Add magnesium stearate (Item 5) as a premix and mix for 4 minutes.
3. Compress on a suitable press.

EXAMPLE 38

Tablet Formulation (Wet Granulation) of (Z,Z)-11,14-eicosadien-5,8-diynoic acid methyl ester

| Item | Ingredients | mg/tablet | | | | |
|---|---|---|---|---|---|---|
| | | 0.1 | 0.5 | 5.0 | 10.0 | 25.0 |
| 1. | (Z,Z)-11,14-eicosadien-5,8-diynoic acid methyl ester | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure
1. Mix Items 1–5 in a suitable mixer, granulate with water. Dry, mill.
2. Mix with Item 5 and compress on a suitable press.

EXAMPLE 39

Capsule Formulation of
2-(1-fluorononadec-13(Z)-en-4,7-diynyl)-4,5-dihydro-4,4-dimethyloxazole

| | | mg/capsule | | | | |
|---|---|---|---|---|---|---|
| Item | Ingredients | 0.1 | 0.5 | 5.0 | 10.0 | 25.0 |
| 1. | 2-(1-fluoro-nonadec-13(Z)-en-4,7-diynyl)-4,5-dihydro-4,4-dimethyloxazole | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures
1. Mix Items 1–3 in a suitable mixer. Mill through a suitable mill.
2. Mix with Items 4 and 5 and fill on capsule machine.

EXAMPLE 40

Tablet Formulation (Direct Compression) of
2-(1-fluorononadec-13(Z)-en-4,7-diynyl)-4,5-dihydro-4,4-dimethyloxazole

| | | mg/tablet | | | | |
|---|---|---|---|---|---|---|
| Item | Ingredients | 0.1 | 0.5 | 5.0 | 10.0 | 25.0 |
| 1. | 2-(1-fluoro-nonadec-13(Z)-en-4,7-diynyl)-4,5-dihydro-4,4-dimethyloxazole | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure
1. Mix Items 1–5 in a suitable mixer for 10–15 minutes.
2. Add magnesium stearate (Item 5) as a premix and mix for 4 minutes.
3. Compress on a suitable press.

EXAMPLE 41

Tablet Formulation (Wet Granulation) of
2-(1-fluorononadec-13(Z)-en-4,7-diynyl)-4,5-dihydro-4,4-dimethyloxazole

| | | mg/tablet | | | | |
|---|---|---|---|---|---|---|
| Item | Ingredients | 0.1 | 0.5 | 5.0 | 10.0 | 25.0 |
| 1. | 2-(1-fluoro-nonadec-13(Z)-en-4,7-diynyl)-4,5-dihydro-4,4-dimethyloxazole | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure
1. Mix Items 1–5 in a suitable mixer, granulate with water. Dry, mill.
2. Mix with Item 5 and compress on a suitable press.

EXAMPLE 42

Capsule Formulation of
(Z)-2-(13-Nonadecene-4,7-diynyl)-4,5-dihydro-4,4-dimethyloxazole

| | | mg/capsule | | | | |
|---|---|---|---|---|---|---|
| Item | Ingredients | 0.1 | 0.5 | 5.0 | 10.0 | 25.0 |
| 1. | (Z)-2-(13-nonadecen-4,7-diynyl)-4,5-dihydro-4,4-dimethyl-oxazole | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures
1. Mix Items 1–3 in a suitable mixer. Mill through a suitable mill.
2. Mix with Items 4 and 5 and fill on capsule machine.

EXAMPLE 43

Tablet Formulation (Wet Granulation) of
(Z)-2-(13-nonadecene-4,7-diynyl)-4,5-dihydro-4,4-dimethyloxazole

| | | mg/tablet | | | | |
|---|---|---|---|---|---|---|
| Item | Ingredients | 0.1 | 0.5 | 5.0 | 10.0 | 25.0 |
| 1. | (Z)-2-(13-nonadecene-4,7-diynyl)-4,5-dihydro-4,4-dimethyl-oxazole | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure
1. Mix Items 1–5 in a suitable mixer, granulate with water. Dry, mill.
2. Mix with Item 5 and compress on a suitable press.

We claim:
1. A compound of the formula

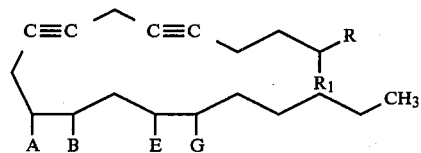

wherein R is

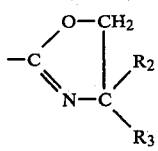

$R_1$ is hydrogen or fluoro; A and B are individually hydrogen or taken together from a carbon to carbon bond with a cis configuration; E and G are individually hydrogen or taken together form a carbon to carbon bond with a cis configuration with the proviso that at least one of A and B taken together or E and D taken together form a carbon to carbon bond with a cis configuration; and $R_2$ and $R_3$ are hydrogen or lower alkyl; or pharmaceutically acceptable salts thereof.

2. The compound of claim 1 where $R_1$ is hydrogen.
3. The compound of claim 2 wherein said compound is (Z)-2-(13-nonadecene-4,7-diynyl)-4,5-dihydro-4,4-dimethyloxazole.
4. The compound of claim 2 where $R_1$ is fluoro.
5. The compound of claim 4 wherein said compound is 2-(1-fluorononadec-13(Z)-en-4,7-diynyl)-4,5-dihydro-4,4-dimethyloxazole.
6. A compound of the formula

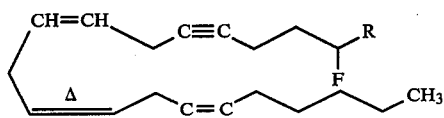

wherein R is

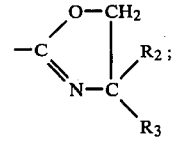

and $R_2$ and $R_3$ are hydrogen; and Δ designates a cis double bond.

7. The compound of claim 5 wherein said compound is 2-[1-fluorononadeca-7(Z),10(Z),13(Z)-trien-4-ynyl]-4,5-dihydro-4,4-dimethyloxazole.
8. A compound of the formula:

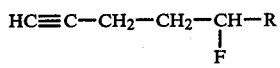

wherein R is

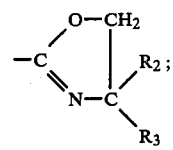

$R_1$ is hydrogen, alkali metal, alkaline earth metal, or lower alkyl; and $R_2$ and $R_3$ are hydrogen or lower alkyl, or magnesium halide salts thereof.

9. The compound of claim 8 wherein said compound is 2-(1-fluoro-4-pentynyl)-4,5-dihydro-4,4-dimethyloxazole.

* * * * *